US010541107B2

(12) United States Patent
Fujiyoshi et al.

(10) Patent No.: US 10,541,107 B2
(45) Date of Patent: Jan. 21, 2020

(54) THREE-DIMENSIONAL IMAGE RECONSTRUCTION METHOD, IMAGE PROCESSOR, AND TRANSMISSION ELECTRON MICROSCOPE, USING IMAGE OBTAINED BY TILTED ELECTRON BEAM CONDITIONS

(71) Applicants: National University Corporation Nagoya University, Nagoya-shi (JP); JEOL Ltd., Tokyo (JP)

(72) Inventors: Yoshinori Fujiyoshi, Nagoya (JP); Isamu Ishikawa, Tokyo (JP); Naoki Hosogi, Tokyo (JP)

(73) Assignees: National University Corporation Nagoya University, Aichi (JP); JEOL Ltd., Tokyo (JP)

( * ) Notice: Subject to any disclaimer, the term of this patent is extended or adjusted under 35 U.S.C. 154(b) by 0 days.

(21) Appl. No.: 15/505,462

(22) PCT Filed: Aug. 21, 2015

(86) PCT No.: PCT/JP2015/073604
§ 371 (c)(1),
(2) Date: Feb. 21, 2017

(87) PCT Pub. No.: WO2016/027895
PCT Pub. Date: Feb. 25, 2016

(65) Prior Publication Data
US 2017/0278669 A1  Sep. 28, 2017

(30) Foreign Application Priority Data
Aug. 22, 2014 (JP) .................................. 2014-169003

(51) Int. Cl.
*H01J 37/22* (2006.01)
*H01J 37/26* (2006.01)
*G01N 23/04* (2018.01)

(52) U.S. Cl.
CPC ............ *H01J 37/222* (2013.01); *G01N 23/04* (2013.01); *H01J 37/261* (2013.01)

(58) Field of Classification Search
None
See application file for complete search history.

(56) References Cited

U.S. PATENT DOCUMENTS

| 6,604,052 B1 * | 8/2003 | Jensen | G06K 9/00134 |
| | | | 435/6.11 |
| 2009/0283676 A1 * | 11/2009 | Skoglund | G01N 23/046 |
| | | | 250/307 |

(Continued)

FOREIGN PATENT DOCUMENTS

| JP | 200741738 A | 2/2007 |
| JP | 2008134212 A | 6/2008 |

(Continued)

OTHER PUBLICATIONS

ISR re PCT/JP2015/073604 dated Nov. 24, 2015.

(Continued)

*Primary Examiner* — James Choi
(74) *Attorney, Agent, or Firm* — The Webb Law Firm

(57) ABSTRACT

A three-dimensional image reconstruction method associated with the present invention includes the steps of: obtaining a first transmission electron microscope image of a sample containing the membrane proteins present within a lipid membrane, the image having been taken by illuminating an electron beam on the sample from a direction tilted relative to a line normal to the membrane surface of the lipid membrane; obtaining a second transmission electron microscope image of the sample taken by illuminating the electron (Continued)

beam on the sample perpendicularly to the membrane surface of the lipid membrane; identifying orientations of the membrane proteins of the first transmission electron microscope image on a basis of the second transmission electron microscope image; and analyzing a three-dimensional structure of the membrane proteins from the first transmission electron microscope image on a basis of information about the identified orientations of the membrane proteins.

7 Claims, 10 Drawing Sheets

(56) References Cited

U.S. PATENT DOCUMENTS

| | | |
|---|---|---|
| 2010/0067809 A1 | 3/2010 | Kawata et al. |
| 2012/0120226 A1* | 5/2012 | de Jonge ............ G01N 23/2204 348/80 |

FOREIGN PATENT DOCUMENTS

| | | |
|---|---|---|
| JP | 2012209050 A | 10/2012 |
| WO | 2007114772 A1 | 10/2007 |

OTHER PUBLICATIONS

Radermacher, "Three-Dimensional Reconstruction of Single Particles From Random and Nonrandom Tilt Series", Journal of Electron Microscopy Technique, Feb. 2005, pp. 359-394, vol. 9, No. 4.

Ueno et al., "Single Particle Analysis of Proteins by Electron Microscopy", The Journal of the Physical Society of Japan, Aug. 2002, pp. 568-574, vol. 57, No. 8.

Henderson et al., Tilt-pair analysis of images from a range of different specimens in single-particle electron cryomicroscopy, J Mol Biol., Nov. 2011, pp. 1028-1046, vol. 413, No. 5.

Extended European Search Report for application No. 15833770.9 dated Jan. 17, 2018.

Radermacher, Michael; "Three-Dimensional Reconstruction of Single Particles From Random and Nonrandom Tilt Series"; Journal of Electron Microscopy Technique, 1988, pp. 359-394; vol. 9.

Japanese Office Action issued in JP2016-544270 dated Dec. 12, 2008.

Penczek et al., Three-dimensional reconstruction of single particles embedded in ice, Ultramicroscopy, Jan. 1992, pp. 33-53, vol. 40, No. 1.

van Heel et al., Single-particle electron cryo-microscopy: towards atomic resolution, Quarterly Reviews of Biophysics, Cambridge University Press, Nov. 2000, pp. 307-369, vol. 33, No. 4.

Zampighi et al., The Kohonen self-organizing map: a tool for the clustering and alignment of single particles images using random conical tilt, Journal of Structural Biology, Academic Press, Jun. 2004, pp. 368-380, vol. 146, No. 3.

European Office Action issued in EP 15833770.9 dated Aug. 20, 2019.

\* cited by examiner

THREE-DIMENSIONAL IMAGE RECONSTRUCTION METHOD, IMAGE PROCESSOR, AND TRANSMISSION ELECTRON MICROSCOPE, USING IMAGE OBTAINED BY TILTED ELECTRON BEAM CONDITIONS

CROSS-REFERENCE TO RELATED APPLICATIONS

This application is the United States national phase of International Application No. PCT/JP2015/073604 filed Aug. 21, 2015, and claims priority to Japanese Patent Application No. 2014-169003 filed Aug. 22, 2014, the disclosures of which are hereby incorporated in their entirety by reference.

TECHNICAL FIELD

The present invention relates to a three-dimensional (3D) image reconstruction method, image processor, and electron microscope.

BACKGROUND ART

Three methods, i.e., structural analysis using a two-dimensional crystal based on electron crystallography, single particle analysis, and electron tomography, are known as methods of performing structural analysis of biological samples using an electron microscope.

In a structural analysis using a two-dimensional crystal based on electron crystallography, three-dimensional structures are analyzed by obtaining electron diffraction patterns and electron microscope images (bright-field images) from a sample tilted at various tilt angles (e.g., 0°, 20°, 45°, 60°, and so on), calculating amplitude data from the intensities of the electron diffraction patterns at diffraction points, and calculating phase data from the electron microscope images. Where a good two-dimensional crystal is obtained, the use of electron crystallography allows for analysis up to a high resolution of 1.9 Å. At such high resolution, the structure of membrane proteins as well as detailed structures including lipid molecules and water molecules can be analyzed.

The method of single particle analysis is a technique of reconstructing the three-dimensional structure of a molecule by image processing from electron microscope images of the particles of isolated biological macromolecules, such as protein molecules (see, for example, patent literature 1).

In methods of single particle analysis, the structures of membrane proteins such as TRP (Transient Receptor Potential) channels have been structurally analyzed in recent years at a resolution of 3.4 Å. In single particle analysis, three-dimensional structures of membrane proteins can be analyzed at such a high resolution that an atomic model can be generated without crystallization.

The development of methods of single particle analysis of recent years has been brought about by the revolutionary development in an apparatus for recording images, as well as by development of stable cryoelectron microscopes. One technique had been employed is to record electron microscope images on film. Another technique consists of converting an electron beam into light by a fluorescent agent and recording the light with a camera using CCDs (charge coupled devices) or the like. On the other hand, in recent years, there has been developed an apparatus wherein an electron beam is directly recorded in a CMOS (Complementary MOS) camera or the like, and the recording method has been improved. This has greatly improved both the DQE (Detectable Quantum Efficiency) and the MTF (Modulation Transfer Function). Owing to such instrumental development, it has become possible to record high-resolution images at extremely high efficiency. Such technical evolution has allowed for high-resolution structural analysis of even membrane proteins without producing crystals by the use of a method of single particle analysis.

However, in structural analysis of TRP using single particle analysis, there is the problem that, if detergents are used, micelles create serious background noise. Therefore, in structural analysis of TRP, micelles have been removed by replacing the surfactant by amphipols. In the case of TRP, the surfactant can be successfully replaced by amphipols but this replacement is not always generally feasible.

Electron tomography is a technique of reconstructing a three-dimensional structure by tilting a sample in small angular increments (i.e., tilting it almost continuously), taking a number of electron microscope images, and image processing them (see, for example, patent literature 2). If electron tomography is used, three-dimensional morphologies of complex structures can be analyzed. However, it is difficult to improve the SN ratio by averaging many molecules such as methods of structural analyses of single particle analysis and electron crystallography. Under the present situation, therefore, it is difficult to make analyses at resolutions higher than 30 Å.

As described so far, three kinds of methods are used for high-resolution structural analysis using an electron microscope. Especially, methods of single particle analysis are attracting much attention. The reason why methods of single particle analysis are attracting attention is that a three-dimensional structure can be analyzed even if an effort to achieve crystallization, which is not certain to succeed, is not made and that analysis at resolutions higher than 3.5 Å is possible, it being noted that at this resolution of 3.5 Å, an atomic model can be created. Consequently, methods of single particle analysis have received much expectation and attention in research areas including many applications typified by structural researches for drug discovery, as well as in development of fundamental biological researches.

CITATION LIST

Patent Literature

Patent literature 1: JP-A-2007-41738
Patent literature 2: JP-A-2012-209050

SUMMARY OF INVENTION

Solution to Problem

However, where an attempt is made to analyze the structure of an important membrane protein as a target of drug discovery by the use of a method of single particle analysis, an important issue remains.

Structural analysis using a method of single particle analysis of membrane proteins is carried out either by covering the hydrophobic portions of the membrane proteins with a surfactant so as to solubilize them or by replacing the surfactant with amphipols. Therefore, it follows that the structure is analyzed under the state where membrane proteins do not exist within the lipid membrane although the membrane proteins should function intrinsically within this membrane. Structural analysis and research on membrane proteins conducted heretofore has revealed that it is important to structurally analyze membrane proteins while they are present within a lipid membrane in which the proteins should function intrinsically.

For example, the structures of water channels and aquaporin-4 which have been confirmed to express themselves in large quantities in the brain have been analyzed at a resolution of 2.8 Å by electron crystallography. In this analysis by electron crystallography, water molecules within the channel are observed to be clearly discriminated. Although analyzed at a higher resolution of 1.8 Å, the maps of water molecules are blurred in the structure of the same aquaporin-4 that was analyzed by X-ray crystallographic structural analysis. Thus, it has been impossible to observe water molecules to be separate from each other.

The reason is considered as follows. In X-ray crystallographic structural analysis, the structure was analyzed while lipid molecules have been dissolved away by detergents, reducing an electrostatic (dielectric constant) distribution that is characteristic of the lipid membrane. This weakens the electrostatic field due to dipole moments of short helices, thus losing the orientations of the water molecules within the water channel. The electrostatic field formed by such short helixes is observed in water channels. Furthermore, this field plays an important role in other ion channels.

A membrane protein forms its structure while under pressure from a side of the lipid membrane. Therefore, where the pressure by the lipid membrane does not exist, the protein is in danger of being altered in structure or denatured.

As described so far, it is necessary to know the structure of membrane proteins while present within lipid membranes in which they function intrinsically. In a method of single particle analysis, the hydrophobic portions of the membrane proteins are covered with detergents so as to become solubilized as mentioned previously. An image of a state in which they are dispersed within a buffer is taken, and the structure is analyzed. Therefore, in a method of single particle analysis, it is difficult to analyze the intrinsic functional structure in a manner similar to analysis by electron crystallography.

FIG. 13 is a view showing the state of membrane proteins 4 when they are solubilized using detergents and a single particle analysis is performed. Where a single particle analysis of the membrane proteins 4 is performed using detergents, it is difficult to make a precise structural analysis of the membrane proteins 4 because the detergent d forms micelles m, resulting in a high level of background noise as shown in FIG. 13. Therefore, in the single particle analysis of recent years which has succeeded in structural analysis at high resolution, the detergents are replaced by amphipols as described previously. However, there exist membrane proteins for which this replacement cannot be performed easily. There is a desire for a novel technique in order to promote single particle analysis of membrane proteins for which such replacement can be done with difficulty.

In the first place, with respect to many membrane proteins, if they are dissolved away from lipid membranes with detergents and purified, they are denatured. This makes it difficult to structurally analyze them. In order to conduct research on the structures of such unstable membrane proteins, it is desirable that structural analysis can be performed without solubilizing them with detergents.

In view of the problems described so far, the present invention has been made. One object associated with some aspects of the present invention is to provide a three-dimensional image reconstruction method and image processor capable of building up a three-dimensional structural model of membrane proteins present within a lipid membrane. Another object associated with some aspects of the present invention is to provide a transmission electron microscope including the above-described image processor.

Solution to Problem (1) A three-dimensional image reconstruction method associated with the present invention is intended to construct a three-dimensional structural model of membrane proteins, the method comprising the steps of:

obtaining a first transmission electron microscope image of a sample taken by illuminating an electron beam on the sample containing the membrane proteins present within a lipid membrane from a direction tilted relative to a line normal to a membrane surface of the lipid membrane;

obtaining a second transmission electron microscope image of the sample taken by illuminating the electron beam on the sample perpendicularly to the membrane surface of the lipid membrane;

identifying the orientations of the membrane proteins in the first transmission electron microscope image on a basis of the second transmission electron microscope image; and reconstructing a three-dimensional image of the membrane proteins from the first transmission electron microscope image on a basis of information about the identified orientations of the membrane proteins.

In this method of reconstructing a three-dimensional structural model, a three-dimensional structural model of membrane proteins can be reconstructed by identifying the orientations of the membrane proteins in the first transmission electron microscope image taken by illuminating an electron beam from a direction tilted relative to a line normal to the membrane surface of the lipid membrane on a basis of the second transmission electron microscope image taken by illuminating the electron beam perpendicularly to the membrane surface of the lipid membrane. Consequently, in this method of reconstructing a three-dimensional image, a three-dimensional structural model of the membrane proteins present within the lipid membrane can be built up.

(2) In the three-dimensional image reconstruction method associated with the present invention, during the step of constructing a three-dimensional structural model of said membrane proteins, the three-dimensional structural model of said membrane proteins may be reconstructed by extracting a plurality of particle images of the membrane proteins from said first transmission electron microscope image, classifying the extracted particle images according to the orientations of the membrane proteins, and averaging the classified particle images.

In this method of reconstructing a three-dimensional structural model, the three-dimensional structural model is built up by averaging the particle images that have been classified according to the orientations of the membrane proteins. Therefore, the SN ratio of the particle images for constructing the three-dimensional image can be improved. Consequently, a high-resolution three-dimensional structure can be reconstructed.

(3) The three-dimensional image reconstruction method associated with the present invention further comprises the steps of:

obtaining a third transmission electron microscope image of said sample taken by illuminating said electron beam on said sample from a direction tilted at an angle different from that assumed when said first transmission electron microscope image was taken relative to the line normal to the membrane surface of said lipid membrane; and identifying the orientations of said membrane proteins in the third transmission electron microscope image on a basis of said second transmission electron microscope image.

In the step of reconstructing a three-dimensional structural model of the membrane proteins, the three-dimensional structural model of the membrane proteins may be reconstructed from both the first transmission electron microscope image and the third transmission electron microscope image on a basis of information about the identified orientations of the membrane proteins.

In this three-dimensional image reconstruction method, a three-dimensional structural model can be reconstructed from the first transmission electron microscope image and the third transmission electron microscope image for which the incident angle of the electron beam is different from each other. Hence, a three-dimensional image of higher resolution can be reconstructed.

(4) In the three-dimensional reconstruction method associated with the present invention, the dose of said electron beam on said sample assumed when said second transmission electron microscope image is taken may be greater than the dose of the electron beam on the sample assumed when said first transmission electron microscope image is taken.

In this three-dimensional image reconstruction method, it is possible to obtain the second transmission electron image that can be taken under focal conditions different from those under which the first transmission electron microscope image is taken, in order to achieve high contrast. Furthermore, the first transmission electron microscope image causing less sample damage can be obtained.

(5) In the three-dimensional image reconstruction method associated with the present invention, said second transmission electron microscope image may be taken after said first transmission electron microscope image is taken.

In this three-dimensional image reconstruction method, it is possible to obtain the first transmission electron microscope image causing less sample damage, for example, than where the first transmission electron microscope image is taken after the second transmission electron microscope image is taken.

(6) An image processor associated with the present invention is intended to reconstruct a three-dimensional structural model of membrane proteins and comprises:

a first image acquisition portion for obtaining a first transmission electron microscope image of a sample containing said membrane proteins present within a lipid membrane, the image having been taken by illuminating an electron beam on the sample from a direction tilted relative to a line normal to a membrane surface of the lipid membrane;

a second image acquisition portion for obtaining a second transmission electron microscope image of the sample, the second transmission electron microscope image having been taken by illuminating the electron beam on the sample perpendicularly to the membrane surface of the lipid membrane;

an orientation identification portion for identifying the orientations of the membrane proteins in the first transmission electron microscope image on a basis of the second transmission electron microscope image; and a 3D image reconstructing portion for reconstructing a three-dimensional image of the membrane proteins from the first transmission electron microscope image on a basis of information about the identified orientations of the membrane proteins.

This image processor can reconstruct a three-dimensional structural model of membrane proteins by identifying the orientations of the membrane proteins in the first transmission electron microscope image on a basis of the second transmission electron microscope image taken by illuminating the electron beam perpendicularly to the membrane surface of the lipid membrane, the first transmission electron microscope image having been taken by illuminating the electron beam from a direction tilted relative to a line normal to the membrane surface of the lipid membrane. Therefore, this image processor can reconstruct a three-dimensional structural model of membrane proteins present within the lipid membrane.

(7) In the image processor associated with the present invention, said 3D image reconstructing portion may reconstruct a three-dimensional (3D) structural model of the membrane proteins by extracting a plurality of particle images of the membrane proteins from said first transmission electron microscope image, classifying the extracted particle images according to the orientations of the membrane proteins, and averaging the classified particle images.

In this image processor, a three-dimensional structural model is reconstructed by averaging the particle images which have been classified according to the orientations of the membrane proteins. Therefore, the SN ratio of the particle images for reconstructing a three-dimensional structural model can be improved. In consequence, a high-resolution three-dimensional structural model can be built up.

(8) The image processor associated with the present invention further comprises a third image acquisition portion for obtaining a third transmission electron microscope image of said sample taken by illuminating the electron beam on said sample from a direction tilted at an angle different from that assumed when said first transmission electron microscope image was taken relative to the line normal to the membrane surface of said lipid membrane. The orientation identification portion may identify the orientations of the membrane proteins in the third transmission electron microscope image on a basis of the second transmission electron microscope image. The 3D image reconstructing portion may construct a three-dimensional structural model of the membrane proteins from both the first transmission electron microscope image and the third transmission electron microscope image on a basis of information about the identified orientations of the membrane proteins.

In this image processor, a three-dimensional image can be reconstructed from the first transmission electron microscope image and the third transmission electron microscope image for which the incident angle of the electron beam is different from each other. Consequently, a three-dimensional structural model of higher resolution can be built up.

(9) An electron microscope associated with the present invention includes an image processor associated with the present invention.

Since this electron microscope includes an image processor associated with the present invention, a three-dimensional structural model of membrane proteins present within a lipid membrane can be built up.

DESCRIPTION OF EMBODIMENTS

The preferred embodiments of the present invention are hereinafter described in detail using the drawings. It is to be noted that the embodiments given below are not intended to unduly restrict the content of the present invention set forth in the claims and that all the configurations described below are not always essential constituent elements of the invention.

1. First Embodiment 1.1. Sample

Figure 1:
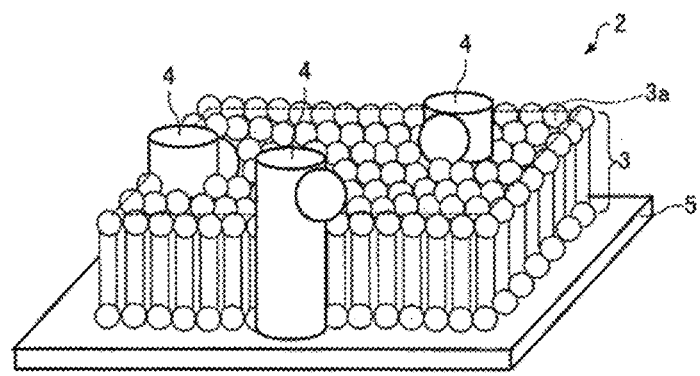
FIG. 1 is a perspective view schematically showing a sample.
Figure 2:
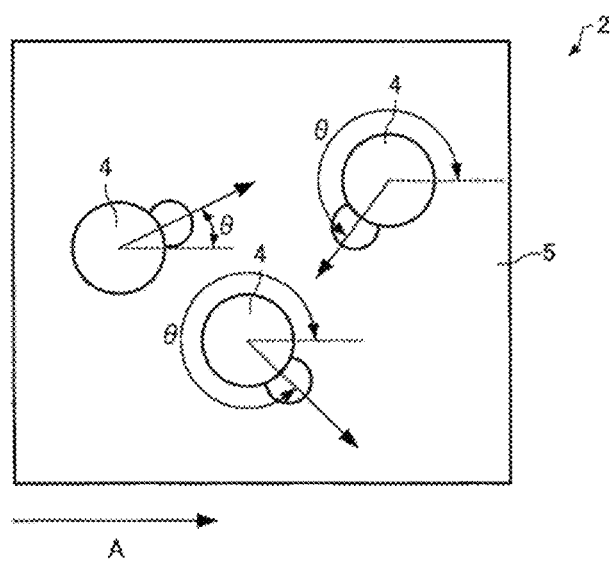
FIG. 2 is a plan view schematically showing the sample.

A sample that is a subject of a structural analysis (reconstruction of a three-dimensional image) is first described. FIG. 1 is a perspective view schematically showing a sample 2 that is the subject of the structural analysis. FIG. 2 is a plan view schematically showing the sample 2. In FIG. 2, for the sake of convenience, a lipid membrane 3 is omitted from being shown.

The sample 2 contains membrane proteins 4 that are present within the lipid membrane (lipid bilayer membrane) 3. As shown in FIG. 1, the membrane proteins 4 exist vertically to a membrane surface 3a (e.g., the top surface of the lipid membrane 3) of the lipid membrane 3 within the lipid membrane 3. The membrane proteins 4 extend through the lipid membrane 3 in a direction vertical to the membrane surface 3a of the lipid membrane 3. Particles of the membrane proteins 4 are orientated in various directions as shown in FIG. 1 and FIG. 2. That is, the particles of the membrane proteins 4 rotate at random relative to an axis vertical to the membrane surface 3a of the lipid membrane 3. Also, the adjacent particles are spaced apart by random spacing. The arrows in FIG. 2 indicate the orientations of the particles of the membrane proteins 4. For example, as shown in FIG. 2, the angle θ made between an axis (arrow) indicating the orientation of each particle of the membrane proteins 4 and an axis A in an arbitrary direction assumes various magnitudes. It can also be said that the angle θ is the angle of rotation of each particle of the membrane proteins 4 with respect to the axis perpendicular to the membrane surface 3a of the lipid membrane 3. The orientations (orientations of the particles) of the membrane proteins 4 can also be represented by the angle of rotation θ.

The sample 2 is obtained, for example, by purifying the membrane proteins 4 using detergents, adding lipid molecules to the purified membrane proteins 4, removing the detergents by dialysis or dilution method, and reconstructing the lipid membrane 3 so as to create lipid membrane fragments including the membrane proteins 4 that are dispersed sparsely within the lipid membrane 3.

Preferably, the sample 2 is obtained by purifying the membrane proteins 4 such that the membrane proteins 4 are dispersed sparsely within the lipid membrane 3 as described previously. The degree of dispersion of the membrane proteins 4 can be controlled by adjusting the mixture ratio between lipid and proteins i.e., LRP (lipid protein ratio)

Furthermore, the sample 2 may be membrane fragments in which the membrane proteins 4 are dispersed under conditions where they are relatively close to each other but do not show crystallinity. In addition, the sample 2 may be membrane proteins that have not been purified with detergents.

The sample 2 is supported by a carbon film 5. Preferably, the carbon film 5 is flat on an atomic level.

The sample 2 is embedded in ice, for example. In particular, the sample 2 is first adsorbed onto the carbon film 5 that has been prepared on a cleavage plane of mica by vacuum evaporation without causing a spark, and extra buffer solution is absorbed with filter paper. The sample 2 is embedded in ice by plunging the sample 2 absorbed in the carbon film 5 into liquid ethane and quickly freezing it. The sample 2 embedded in ice is mounted on a sample stage (cooling stage) of an electron microscope.

1.2. Image Processor and Electron Microscope

Figure 3:
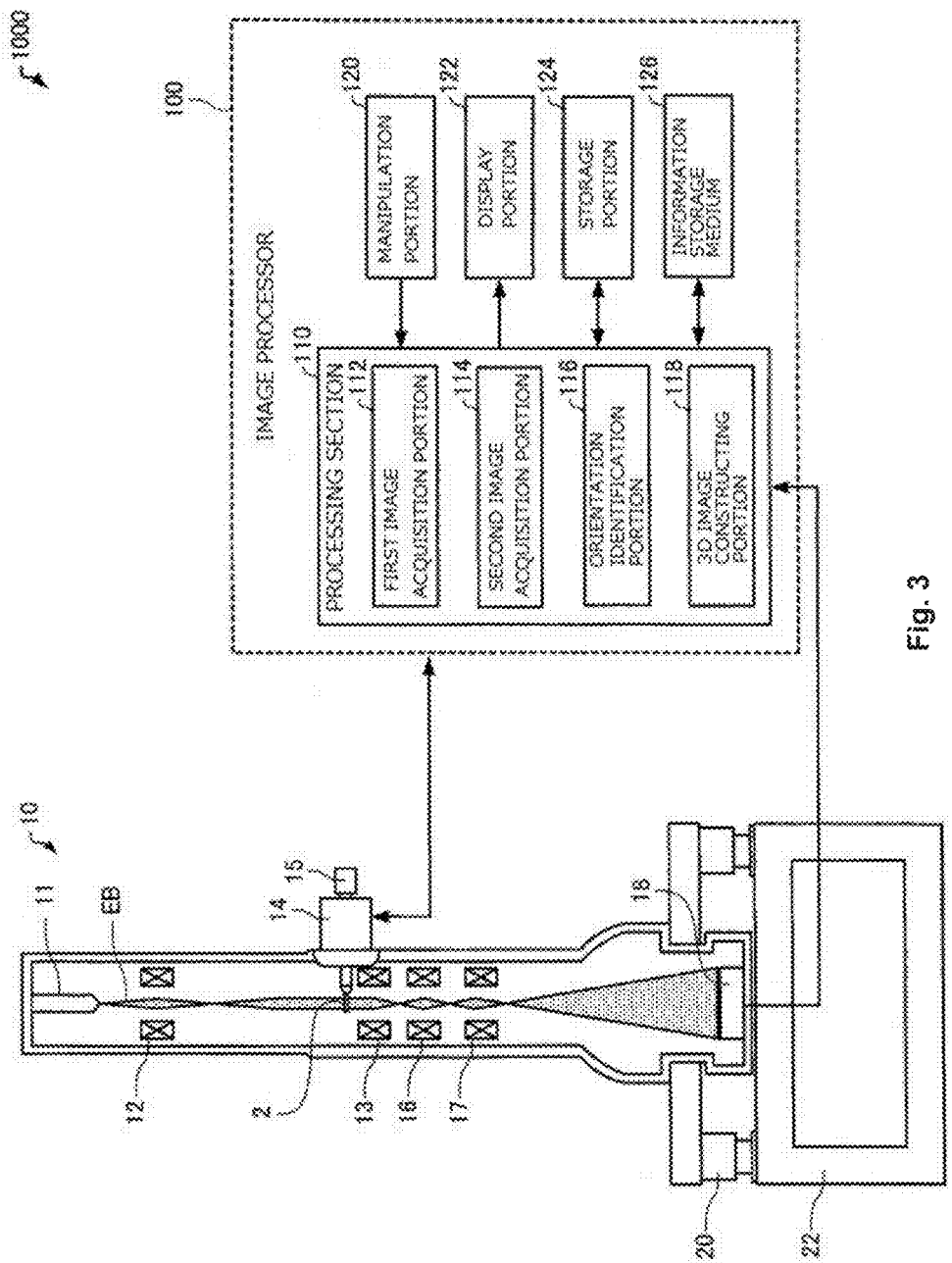
FIG. 3 is a view schematically showing the configuration of an electron microscope including an image processor associated with a first embodiment.

An electron microscope 1000 including the image processor associated with the first embodiment is next described by referring to drawings. FIG. 3 is a view schematically showing the configuration of the electron microscope 1000 including the image processor 100 associated with the first embodiment.

The body 10 of the electron microscope is a transmission electron microscope. The body 10 of the electron microscope is an instrument for imaging electrons transmitted through the sample 2 to obtain a transmission electron microscope image. An example in which the body 10 of the electron microscope is a transmission electron microscope (TEM) is described now. The body 10 of the electron microscope may also be a scanning transmission electron microscope (STEM).

In the electron microscope 1000, the sample 2 can be cooled to low temperatures. Thus, damage to the sample 2 caused by irradiation by an electron beam EB can be reduced. That is, the electron microscope 1000 is a so-called cryoelectron microscope system.

As shown in FIG. 3, the electron microscope 1000 includes the electron microscope body 10 and the image processor 100.

The electron microscope body 10 includes an electron beam source 11, condenser lenses 12, an objective lens 13, the sample stage, 14, having a tilting mechanism, a sample holder 15, an intermediate lens 16, a projector lens 17, and an imaging portion 18.

The electron beam source 11 produces the electron beam EB. The electron beam source 11 emits the electron beam EB by accelerating electrons, which are emitted from a cathode, by means of an anode. For example, an electron gun can be used as the electron beam source 11. No restriction is imposed on the electron gun used as the electron beam source 11. For example, a thermionic emission type, a thermal field emission type, a cold cathode field-emission type, or other type of electron gun can be used.

The condenser lenses 12 are disposed in a stage following the electron beam source 11 (on the downstream of the electron beam EB). The condenser lenses 12 are lenses for causing the electron beam EB generated by the electron beam source 11 to be focused onto the sample 2. The condenser lenses 12 may be configured including a plurality of lenses (not shown).

The objective lens 13 is disposed in a stage following the condenser lenses 12. The objective lens 13 is an initial stage of lens for focusing the electron beam EB transmitted through the sample 2. The objective lens 13 has an upper polepiece and a lower polepiece (none of which are shown). In the objective lens 13, a magnetic field is produced between the upper polepiece and the lower polepiece to focus the electron beam EB.

The sample stage 14 holds the sample 2. In the illustrated example, the sample stage 14 holds the sample 2 via the sample holder 15. The sample stage 14 places the sample 2, for example, between the upper polepiece and the lower polepiece of the objective lens 13. The sample stage 14 can place the sample 2 in position by moving and stopping the sample holder 15. The sample stage 14 can move the sample 2 in a horizontal direction (direction perpendicular to the direction of travel of the electron beam EB) and in a vertical direction (direction along the direction of travel of the electron beam EB). Furthermore, the sample stage 14 can tilt the sample 2. The sample stage 14 is coupled to the image processor 100. The image processor 100 controls the sample stage 14 such that the sample is moved or tilted.

In the illustrated example, the sample stage 14 is a side-entry stage for inserting the sample 2 from a side of the polepieces (not shown) of the objective lens 13. Alternatively, the sample stage 14 may also be a top-entry stage (not shown) for inserting the sample 2 from above the polepieces.

The sample stage 14 is a cooling stage capable of cooling the sample 2. In the sample stage 14, the sample 2 can be cooled, for example, by introducing liquid nitrogen or liquid helium into the sample holder 15.

The intermediate lens 16 is disposed in a stage subsequent to the objective lens 13. The projector lens 17 is disposed in a stage subsequent to the intermediate lens 16. The intermediate lens 16 and the projector lens 17 further magnify the image focused by the objective lens 13 and focus the image onto the imaging portion 18. In the electron microscope 1000, the objective lens 13, intermediate lens 16, and projector lens 17 constitute an imaging system. The intermediate lens 16 may be configured including a plurality of lenses (not shown).

The imaging portion 18 takes a transmission electron microscope image (TEM image) focused by the imaging system. For example, the imaging portion 18 is a digital camera such as a CCD camera or a CMOS camera. The imaging portion 18 outputs information about the taken transmission electron microscope image to the image processor 100.

In the illustrated example, the electron microscope body 10 is mounted on a pedestal 22 via vibration isolators 20.

The image processor 100 is an apparatus for constructing a three-dimensional image of the membrane proteins 4 on a basis of transmission electron microscope images of the sample 2 taken by the electron microscope body 10. As shown in FIG. 3, the image processor 100 includes a processing section 110, a manipulation portion 120, a display portion 122, a storage portion 124, and an information storage medium 126.

The manipulation portion 120 performs processing for obtaining a manipulation signal responsive to a manipulation performed by a user and sending the signal to the processing section 110. The manipulation portion 120 is made, for example, of buttons, keys, a touch panel display, a microphone, or the like.

The display portion 122 displays images generated by the processing section 110, and its function can be implemented by an LCD, a CRT, or the like. The display portion 122 displays a projected image of the membrane proteins 4 and a three-dimensional structural model generated by the processing section 110.

The storage portion 124 becomes a working area for the processing section 110, and its functions can be implemented by a RAM or the like. The storage portion 124 stores programs, data, and so on to permit the processing section 110 to perform various kinds of computational processing. Furthermore, the storage portion 124 is used as a working area for the processing section 110. The processing section 110 is also used to temporarily store the results of computations executed in accordance with various programs by the processing section 110 and so on.

The information storage medium 126 (computer-readable medium) stores programs, data, and so on. Its function can be implemented by an optical disc (such as a CD or a DVD), a magnetooptical disc (MO), a magnetic disc, a hard disc, magnetic tape, a memory (ROM), or the like. The processing section 110 performs various types of processing of the present embodiment on a basis of programs (data) stored in the information storage medium 126. Programs for causing a computer to operate as various portions of the processing section 110 can be stored in the information storage medium 126.

The processing section 110 performs various types of processing in accordance with the programs stored in the storage portion 124. The processing section 110 functions as a first image acquisition portion 112, a second image acquisition portion 114, an orientation identification portion 116, and a 3D (three-dimensional) image reconstructing portion 118 described below by executing programs stored in the storage portion 124. The functions of the processing section 110 can be implemented by hardware such as various processors (e.g., a CPU or a DSP) or an ASIC (e.g., a gate array) or by a program. At least a part of the processing section 110 may be realized by hardware (dedicated circuits). The processing section 110 includes the first image acquisition portion 112, the second image acquisition portion 114, the orientation identification portion 116, and the 3D image reconstructing portion 118.

The first image acquisition portion 112 obtains a transmission electron microscope image (first transmission electron microscope image; hereinafter may also be referred to as the tilted image), which is taken by illuminating the electron beam EB on the sample 2 from a direction tilted relative to a line normal to the membrane surface 3a of the lipid membrane 3 by accepting image information outputted from the imaging portion 18. For example, the first image acquisition portion 112 obtains a 60°-tilted image that is taken by illuminating the electron beam EB from a direction tilted by 60° relative to the line normal to the membrane surface 3a of the lipid membrane 3. The angle of tilt of the electron beam EB when the tilted image obtained by the first image acquisition portion 112 is taken is not restricted to 60°. For example, it is an arbitrary angle from 0° to 70°.

The second image acquisition portion 114 obtains a transmission electron microscope image (second transmission electron microscope image; hereinafter may also be referred to as the "non-tilted image") that is taken by illuminating the electron beam EB on the same region as the region of the sample 2, from which the tilted image of the sample 2 has been taken, perpendicularly to the membrane surface 3a of the lipid membrane 3 by accepting the image information outputted from the imaging portion 18.

The orientation identification portion 116 identifies the orientations of the membrane proteins 4 in the tilted image on a basis of the non-tilted image. The orientation identification portion 116 identifies the orientations of the particles of the membrane proteins 4 in the tilted image from the orientations of the corresponding particles of the membrane proteins 4 in the non-tilted image. The orientation of each membrane protein 4 is represented, for example, as a rotation (rotational angle θ; see FIG. 2) of each particle of the membrane proteins 4 relative to the axis perpendicular to membrane surface 3a of the lipid membrane 3. That is, the orientation identification portion 116 creates information about the rotational angles θ of the particles of the membrane proteins 4 as information about the orientations of the membrane proteins 4.

The 3D image reconstructing portion 118 is analyzed to give a three-dimensional structural model of the membrane proteins 4 from the tilted image, based on the information about the identified orientations of the membrane proteins 4.

Figure 4:
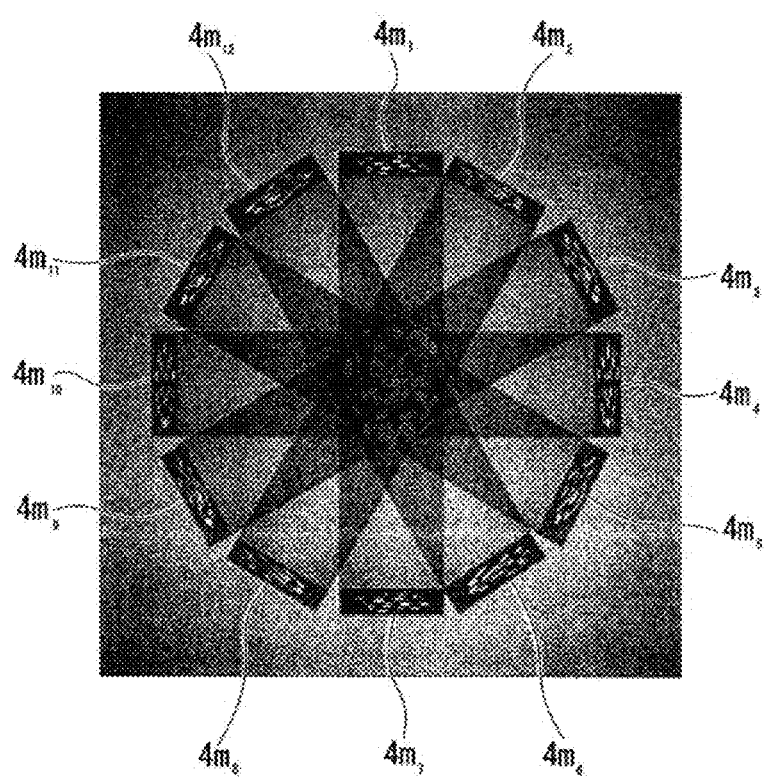
FIG. 4 is a view for illustrating processing performed by a 3D image reconstructing portion of the image processor associated with the first embodiment.

FIG. 4 is a schematic diagram for illustrating the processing of the 3D image reconstructing portion 118. The 3D image reconstructing portion 118 first extracts images of the particles of the membrane proteins 4 from the tilted image, and classifies the extracted particle images according to the orientations of the particles of the membrane proteins 4 (such as angular rotation θ) while taking account of information (such as information about the angular rotation θ) about the orientations of the particles of the membrane proteins 4 identified by the orientation identification portion 116. The reconstructing portion then averages the classified identical, projected particle images, i.e., the particle images which are identical or close in orientation of the membrane proteins 4 (particle images belonging to the same class). Consequently, averaged particle images $4m_1$, $4m_2$, $4m_3$, ... , $4m_n$ (where n is an integer equal to or greater than 2; in the illustrated example, n=12) are obtained for each of the orientations of the membrane proteins 4 (i.e., for each direction of projection). The 3D image reconstructing portion 118 is analyzed to give a three-dimensional structural model of the membrane proteins 4 by a back projection method similar to a method of single particle analysis, using the averaged particle images $4m_1$, $4m_2$, $4m_3$, ... , $4m_n$. Although this schematic diagram (FIG. 4) is drawn planarly for the convenience of drawing, the image is reconstructed in a three-dimensional manner.

Figure 5:
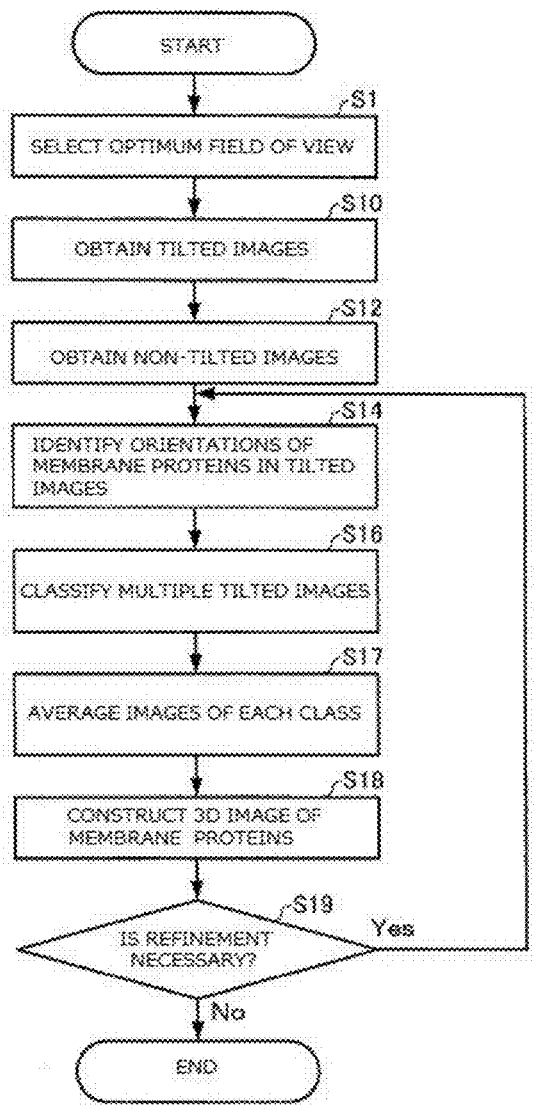
FIG. 5 is a flowchart illustrating one example of a three-dimensional image reconstruction method associated with the first embodiment.

1.3. Method of Constructing 3D Image A method of constructing a three-dimensional structural model of the membrane proteins 4 by the use of the electron microscope 1000 including the image processor 100 associated with the first embodiment is next described by referring to drawings. FIG. 5 is a flowchart illustrating one example of the three-dimensional image reconstruction method associated with the first embodiment.

First, an optimum field of view (sample to be shot) is selected under conditions where the sample is not tilted under low-magnification conditions (e.g., defocused diffraction image conditions) (step S1). Then, the sample is tilted by 60° to permit the 60°-tilted image at the selected sample position can be taken. A tilted image of the sample 2 is obtained which has been taken by illuminating the electron beam EB on the sample 2 from a direction tilted relative to the line normal to the membrane surface 3a of the lipid membrane 3 (step S10). An example in which a 60°-tilted image is obtained is described here.

Figure 6:
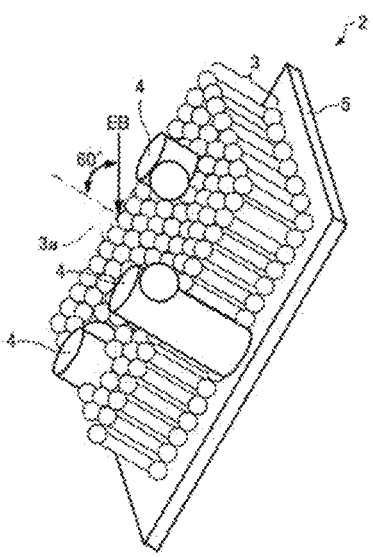
FIG. 6 is a perspective view schematically showing the state of the sample when a 60°-tilted image is taken.

FIG. 6 is a perspective view schematically showing the state of the sample 2 when the 60°-tilted image is taken. The arrows shown in FIG. 6 indicate the direction of incidence of the electron beam EB. The 60°-tilted image is taken under the condition where the sample 2 held to the sample holder 15 is tilted by 60° by the sample stage 14 as shown in FIG. 6. In consequence, the electron beam EB can be illuminated on the sample 2 from a direction tilted by 60° relative to the membrane surface 3a of the lipid membrane 3, so that the 60°-tilted image is obtained.

The first image acquisition portion 112 takes in image information about the 60°-tilted image taken in this way and obtains the 60°-tilted image.

Then, a non-tilted image of the sample 2 is obtained which has been taken by illuminating the electron beam EB on the shot region of the sample 2 perpendicularly to the membrane surface 3a of the lipid membrane 3 (step S12), the shot region having resulted in the 60°-tilted image taken.

Figure 7:
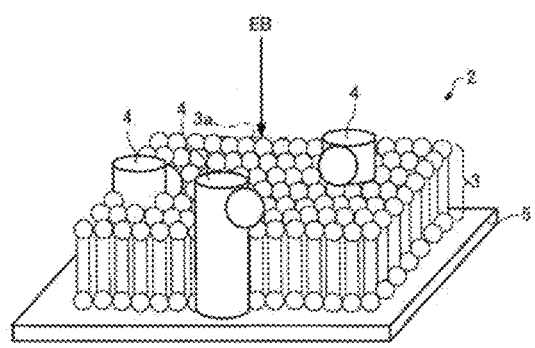
FIG. 7 is a perspective view schematically showing the state of the sample when a non-tilted image is taken.

FIG. 7 is a perspective view schematically showing the state of the sample 2 when the non-tilted image is taken. The arrow shown in FIG. 7 indicates the direction of incidence of the electron beam EB. The non-tilted image is taken, for example, in a horizontal state without the sample stage 14 tilting the sample 2 held to the sample holder 15 as shown in FIG. 7. Consequently, it is possible to illuminate the electron beam EB on the sample 2 from a direction perpendicular to the membrane surface 3a of the lipid membrane 3. The non-tilted image is taken with the same field of view as the 60°-tilted image. The 60°-tilted image and the non-tilted image do not need to be exactly identical in field of view. It suffices that the same region of the sample 2 be contained in both the 60°-tilted image and the non-tilted image.

Shooting is done under conditions where the dose of the electron beam EB on the sample 2 when the non-tilted image is taken is the same as or greater than the dose of the electron beam EB on the sample 2 when the 60°-tilted image is taken.

Where the membrane proteins 4 are membrane proteins having relatively small molecular weights, the contrast of the non-tilted image may be low in some cases, where the non-tilted image is taken under more greatly defocused conditions than the tilted image. Consequently, the non-tilted image can yield high contrast.

Note that the tilted image used for construction of a three-dimensional image is taken under relatively weakly defocused conditions (for example, weaker than in the case of the non-tilted image), because under greatly defocused conditions, vibrations of the contrast transfer function are higher on the high-resolution side.

Figure 8:
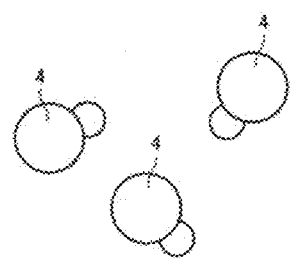
FIG. 8 is a view schematically showing membrane proteins in the non-tilted image.

The second image acquisition portion 114 takes in image information about the non-tilted image taken in this way and obtains the non-tilted image. FIG. 8 is a view schematically showing the membrane proteins 4 in the non-tilted image. As shown in FIG. 8, the non-tilted image is an image of the membrane proteins 4, taken from a direction perpendicular to the membrane surface 3a of the lipid membrane 3.

In this way, the image processor 100 obtains the 60°-tilted image and the non-tilted image, forming a pair, taken with the same field of view. The image processor 100 may derive one pair of 60°-tilted image and non-tilted image or plural pairs of 60°-tilted images and non-tilted images. The 60°-tilted image and non-tilted image may be taken manually by an operator or automatically by a control section (not shown) that controls the electron microscope body 10.

Then, the orientation identification portion 116 identifies the orientations of the membrane proteins 4 in the 60°-tilted image, based on the non-tilted image (step S14).

The orientation identification portion 116 identifies the orientations of the particles of the membrane proteins 4 in the 60°-tilted image from the orientations of the corresponding particles of the membrane proteins 4 in the non-tilted image. The non-tilted image is an image of the membrane proteins 4, taken from a direction perpendicular to the membrane surface 3a of the lipid membrane 3 as shown in FIG. 8. Therefore, the orientations of the particles of the membrane proteins 4, i.e., the rotations (rotational angles θ) of the particles of the membrane proteins 4 relative to an axis perpendicular to the membrane surface 3a of the lipid membrane 3, can be identified precisely.

Then, the 3D image reconstructing portion 118 is analyzed to give a three-dimensional structural model of the membrane proteins 4 from the 60°-tilted image on a basis of information about the identified orientations of the membrane proteins 4.

In particular, the 3D image constructing portion 118 first extracts images (60°-tilted images) of particles of the membrane proteins 4 from the 60°-tilted images, classifies the extracted 60°-tilted images according to the orientation of each particle of the membrane proteins 4 while taking account of information about the orientations of the particles of the membrane proteins 4 identified by the orientation identification portion 116 (step S16), and averages the classified 60° particle images, i.e., 60° particle images which are identical or close in orientation of particles of the membrane proteins 4 (step S17). Consequently, an averaged 60° particle image is obtained for each orientation of particles of the membrane proteins 4 (for each direction of projection). The 3D image reconstructing portion 118 can be analyzed to give a three-dimensional structural model of the membrane proteins 4 by a back projection method or the like in the same way as in a method of single particle analysis, using the averaged 60° particle images (step S18). Then, the 3D image reconstructing portion 118 makes a decision as to whether it is needed to refine the reconstructed three-dimensional structural model (step S19). If the decision is that a refinement is needed (if Yes at step S19), control returns to step S14, and processing of steps S14-S19 is performed. If the decision is that no refinement is needed (if No at step S19), the processing is ended.

Because of the steps described so far, a three-dimensional structural model of the membrane proteins 4 can be obtained.

The 3D image reconstruction method and image processor 100 associated with the first embodiment has the following features, for example.

The three-dimensional image reconstruction method associated with the first embodiment includes the step (step S10) of obtaining a tilted image of the sample 2, the step (step S12) of obtaining a non-tilted image of the sample 2, the step (step S14) of identifying the orientations of the membrane proteins 4 in the tilted image on a basis of the non-tilted image, and the step (step S18) of reconstructing a three-dimensional structural model of the membrane proteins 4 from the tilted image on a basis of information about the identified orientations of the membrane proteins 4. In this way, in the three-dimensional image reconstruction method associated with the first embodiment, a three-dimensional structural model of the membrane proteins 4 can be reconstructed by identifying the orientations of the membrane proteins 4 in the tilted image, based on the non-tilted image. In consequence, a three-dimensional structural model of the membrane proteins 4 present within the lipid membrane 3 can be built up. When needed, the identification of the orientations of the membrane proteins 4 can be refined further by repetitively feeding the results of the reconstruction of the three-dimensional structural model back to step S14. As a result, the resolution at which images can be resolved and the accuracy of analysis can be improved.

Since the non-tilted image is an image taken from a direction perpendicular to the membrane surface 3a of the lipid membrane 3 of the membrane proteins 4, the orientations of the particles of the membrane proteins 4 can be identified more precisely, for example, than the tilted image. Consequently, in the three-dimensional image reconstruction method associated with the first embodiment, a high-resolution three-dimensional structural model can be obtained.

In this way, in the three-dimensional image reconstruction method associated with the first embodiment, a three-dimensional structural model of the membrane proteins 4 present within the lipid membrane 3 can be obtained even when the membrane proteins would be denatured, for example, in the solubilizing process by detergents. That is, in the three-dimensional image reconstruction method associated with the first embodiment, a three-dimensional structural model can be built up without solubilizing and purifying process of the membrane proteins 4.

Figure 9:
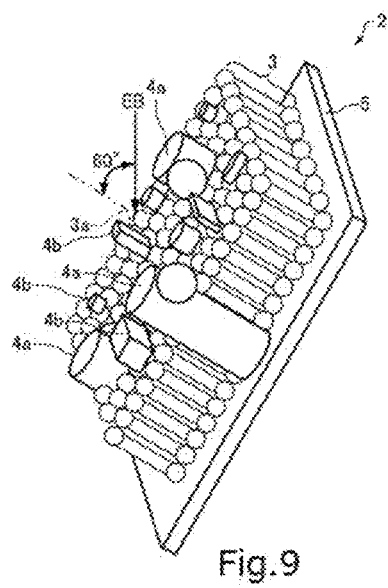
FIG. 9 is a perspective view schematically showing the state of a sample containing unpurified membrane proteins when a 60°-tilted image is taken.
Figure 10:
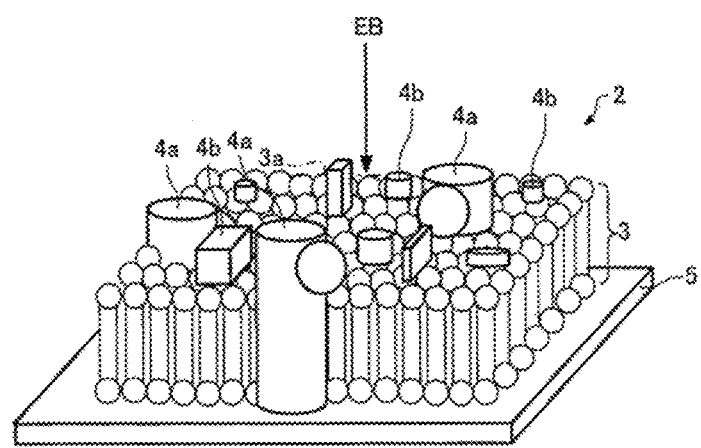
FIG. 10 is a perspective view schematically showing the state of the sample containing the unpurified membrane proteins when a non-tilted image is taken.

FIG. 9 is a perspective view schematically showing the state of the sample 2 including the unpurified membrane proteins 4 when a 60°-tilted image is taken. FIG. 10 is a perspective view schematically showing the state of the sample 2 including the unpurified membrane proteins when a non-tilted image is taken. As shown in FIGS. 9 and 10, if there are many membrane proteins 4b other than a target, then target membrane proteins 4a can be selected from the non-tilted image and a three-dimensional structural model be reconstructed. If there are a variety of membrane proteins, a non-tilted image permits the target membrane proteins 4a to be selected more easily than a tilted image and, therefore, a three-dimensional image of the target membrane proteins 4a can be constructed with greater ease.

In the three-dimensional construction method associated with the first embodiment, during the step (step S18) of reconstructing a three-dimensional image of the membrane proteins 4, plural particle images of the membrane proteins 4 are extracted from the tilted image, the extracted particle images are classified according to the orientations of the membrane proteins 4, the classified particle images are averaged, and a three-dimensional structural model of the membrane proteins 4 is reconstructed. In this way, in the three-dimensional image reconstruction method associated with the first embodiment, a three-dimensional image is reconstructed by averaging the classified particle images and so the SN ratio of the particle images for reconstructing a three-dimensional image can be improved. Hence, a high-resolution three-dimensional structural model can be built up.

Here, the non-tilted image is not used for construction of a three-dimensional image and so tolerates more sample damage than a tilted image. However, high contrast is desirable for identification of the orientations of the membrane proteins 4. Also, the tilted image preferably produces less sample damage because it is used for reconstruction of a three-dimensional image. In the three-dimensional image reconstruction method associated with the first embodiment, a non-tilted image with high contrast and high SN ratio can be obtained by illuminating the dose of the electron beam EB on the sample 2 when a non-tilted image is taken greater than the dose of the electron beam EB on the sample 2 when a tilted image is taken. In addition, a tilted image with less sample damage can be obtained.

Furthermore, in the three-dimensional image reconstruction method associated with the first embodiment, since a non-tilted image is taken after a tilted image is taken, a tilted image with less sample damage can be obtained as compared with the case where a tilted image is taken after a non-tilted image is taken.

In the image processor 100, the orientation identification portion 116 identifies the orientations of the membrane proteins 4 in the tilted image, based on the non-tiled image of the sample 2 including the membrane proteins 4 present within the lipid membrane 3, and the 3D image reconstructing portion 118 is analyzed to give a three-dimensional structural model of the membrane proteins 4 from the tilted image of the sample 2, based on information about the orientations of the membrane proteins 4 identified by the orientation identification portion 116. In this way, in the image processor 100, the orientations of the membrane proteins 4 in the tilted image can be identified based on the non-tilted image and a three-dimensional structural model of the membrane proteins 4 can be constructed. Accordingly, a three-dimensional structural model of the membrane proteins 4 existing within the lipid membrane 3 can be reconstructed.

In the image processor 100, the 3D image reconstructing portion 118 extracts plural particle images of the membrane proteins 4 in a tilted image, classifies the extracted particle images according to each orientation of the membrane proteins 4, averages the classified particle images, and is analyzed to give a three-dimensional structural model of the membrane proteins 4. Therefore, the image processor 100 can build up a high-resolution three-dimensional structural model.

Since the electron microscope 1000 includes the image processor 100, a three-dimensional structural model of the membrane proteins 4 present within the lipid membrane 3 can be reconstructed.

2. Second Embodiment

2.1. Image Processor and Electron Microscope

Figure 11:
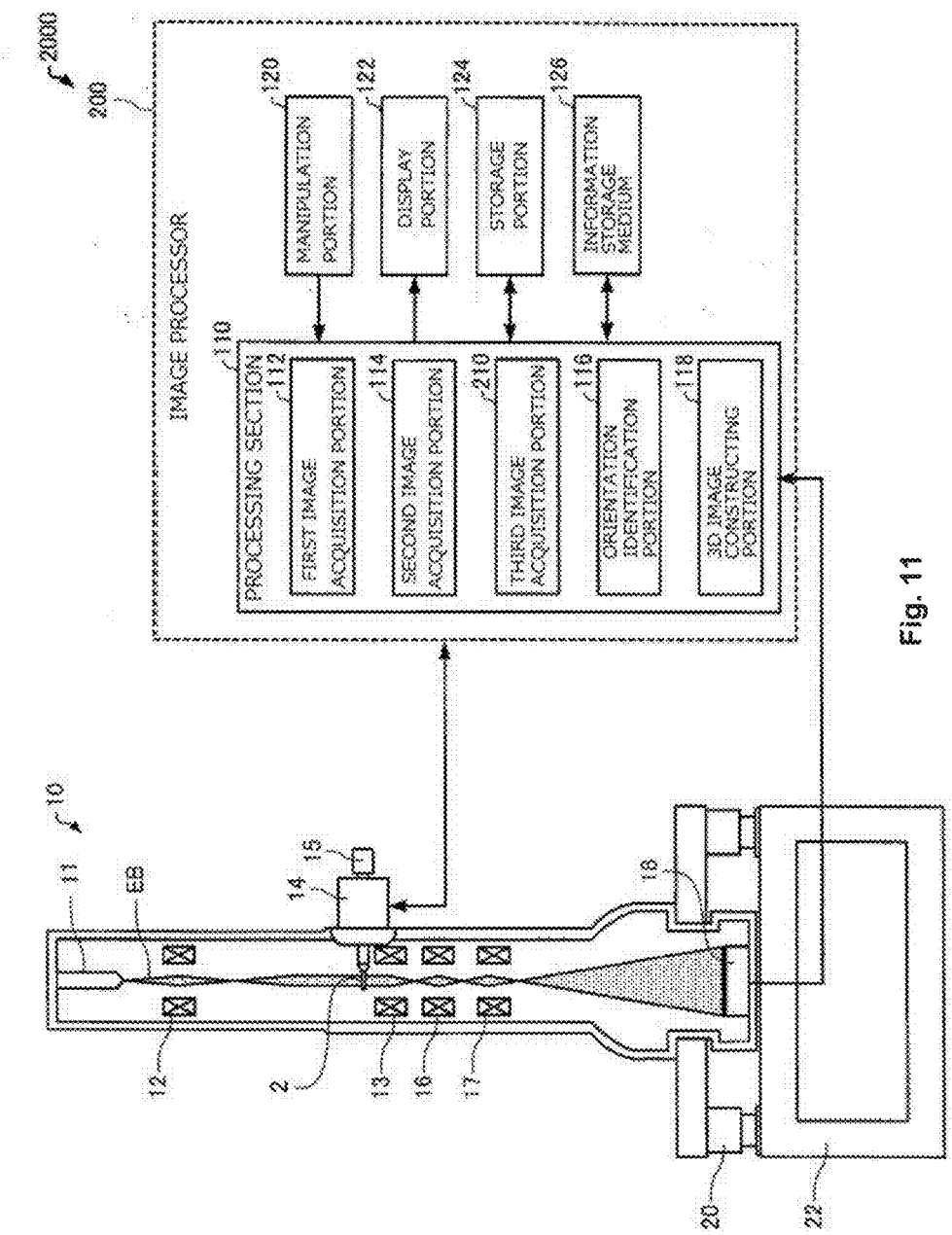
FIG. 11 is a view schematically showing the configuration of an electron microscope including an image processor associated with a second embodiment.

An electron microscope including an image processor associated with a second embodiment is next described by referring to drawings. FIG. 11 is a view schematically showing the configuration of an electron microscope 2000 including the image processor, 200, associated with the second embodiment. In the following, those members of the image processor and electron microscope body associated with the second embodiment which are similar in function with the constituent members of the image processor 100 and electron microscope body 10 associated with the first embodiment are indicated by the same symbols, and their detailed description is omitted.

In the image processor 200, the processing section 110 is configured including a third image acquisition portion 210 as shown in FIG. 11.

The third image acquisition portion 210 obtains a tilted image (third transmission electron microscope image; hereinafter referred to also as the "second tilted image") taken by illuminating the electron beam EB on the sample 2 from a direction tilted at an angle different from that assumed when the tilted image (hereinafter referred to also as the "first tilted image") obtained by the first image acquisition portion 112 relative to a line normal to the membrane surface 3a of the lipid membrane 3, by accepting image information outputted from the imaging portion 18.

For example, the first image acquisition portion 112 obtains a 60°-tilted image taken by illuminating the electron beam EB from a direction tilted by 60° relative to a line normal to the membrane surface 3a of the lipid membrane 3. The third image acquisition portion 210 obtains a 20°-tilted image taken by illuminating the electron beam EB from a direction tilted by 20° relative to the line normal to the membrane surface 3a of the lipid membrane 3.

The second tilted image obtained by the third image acquisition portion 210 is different in field of view from the first tilted image. At this time, the second image acquisition portion 114 obtains both a non-tilted image with the same field of view as the first tilted image and a non-tilted image with the same field of view as the second tilted image. The second tilted image obtained by the third image acquisition portion 210 may be identical in field of view to the first tilted image. The tilt of the electron beam EB when the first tilted image obtained by the first image acquisition portion 112 is taken and the tilt of the electron beam EB when the second tilted image obtained by the third image acquisition portion 210 is taken are not restricted to 60° and 20°.

The orientation identification portion 116 identifies the orientations of the membrane proteins 4 in the first tilted image and the orientations of the membrane proteins 4 in the second tilted image on a basis of non-tilted images. The orientation identification portion 116 identifies the orientations of the particles of the membrane proteins 4 in the second tilted image from the orientations of the corresponding particles of the membrane proteins 4 in the non-tilted image having the same field of view as the second tilted image.

The 3D image reconstructing portion 118 is analyzed to give a three-dimensional structural model of the membrane proteins 4 from the first tilted image and the second tilted image, based on information about the identified orientations of the membrane proteins 4.

The 3D image reconstructing portion 118 first extracts images (particle images) of particles of the membrane proteins 4 from the first tilted image and classifies the extracted particle images according to the orientations of the membrane proteins 4 while taking account of information about the orientations of the particles of the membrane proteins 4 identified by the orientation identification portion 116. The classified particle images, i.e., particle images of the membrane proteins 4 which are identical or close in orientation, are averaged.

Then, the 3D image reconstructing portion 118 extracts images (particle images) of particles of the membrane proteins 4 from the second tilted image, classifies the extracted particle images according to the orientations of the membrane proteins 4 while taking account of information about the orientations of the particles of the membrane proteins 4 identified by the orientation identification portion 116, and averages the classified particle images, i.e., particle images of the membrane proteins 4 which are identical or close in orientation.

Consequently, an averaged particle image is obtained for each orientation of the membrane proteins 4 (i.e., for each direction of projection). The 3D image reconstructing portion 118 is analyzed to give a three-dimensional structural model of the membrane proteins 4 by a back projection method in the same way as in a method of single particle analysis using the averaged particle images.

2. 2. Method of Reconstructing Three-Dimensional Structure

Figure 12:
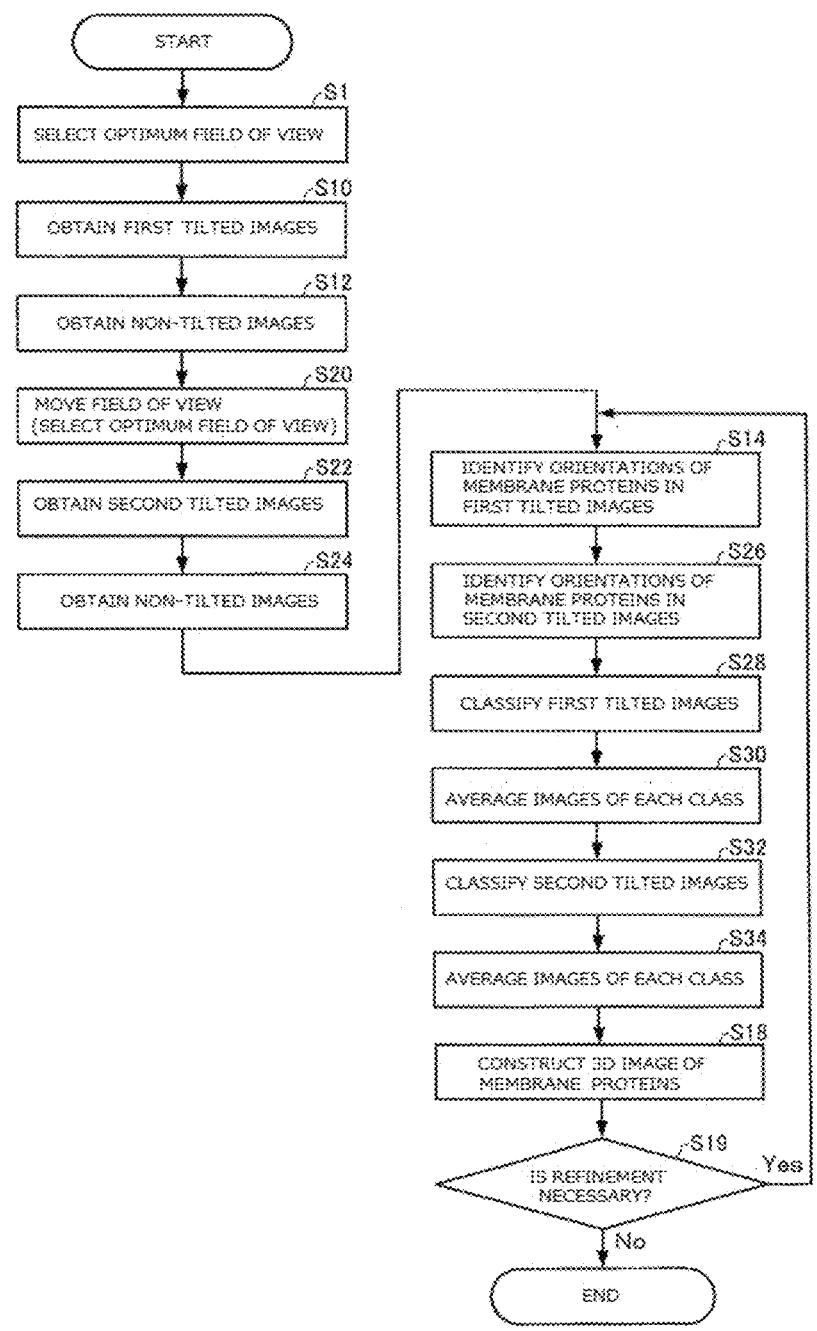
FIG. 12 is a flowchart illustrating one example of a three-dimensional image construction method associated with the second embodiment.
Figure 13:
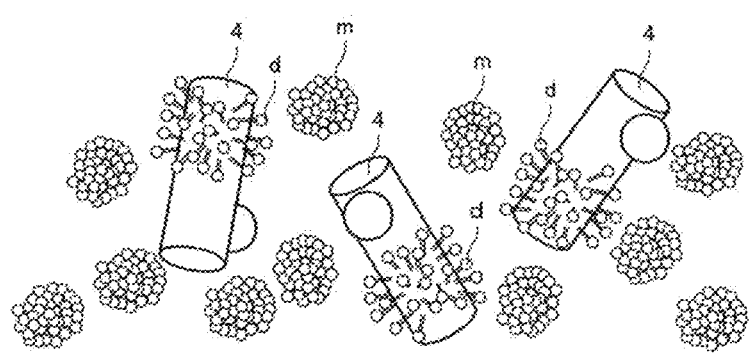
FIG. 13 is a view showing the state of membrane proteins when a single particle analysis is performed by solubilizing the proteins using detergents.

A method of reconstructing a three-dimensional structure of the membrane proteins 4 by the use of the electron microscope 2000 including the image processor 200 associated with the second embodiment is next described by referring to a drawing. FIG. 12 is a flowchart illustrating one example of the three-dimensional image reconstruction method associated with the second embodiment. In the flowchart shown in FIG. 12, those steps similar to the flowchart shown in FIG. 5 are given identical symbols and a detailed description thereof is omitted.

First, an optimum field of view is selected (step S1). This selection of the optimum field of view is made similarly to the processing of step S1 in the above-described first embodiment. Then, the sample is tilted by 60° to permit a 60°-tilted image at the selected sample position to be taken. Then, the first image acquisition portion 112 obtains the first tilted image of the sample 2 (for example, a 60°-tilted image) taken by illuminating the electron beam EB on the sample 2 from a direction tilted relative to a line normal to the membrane surface 3a of the lipid membrane 3 (step S10).

Then, the second image acquisition portion 114 obtains a non-tilted image of the sample 2, taken by illuminating the electron beam EB on the region of the sample 2 perpendicularly to the membrane surface 3a of the lipid membrane 3, the region having resulted in the 60°-tilted image (step S12).

Then, the observed field of view is moved and an optimum field of view is selected in the same way as the processing of step S1 (step S20). The sample 2 is moved by the sample stage 14 to move (vary) the observed field of view. Thus, a region different from the region of the sample 2 from which the 60°-tilted image was taken can be taken in the next step S22.

Then, the third image acquisition portion 210 obtains a second tilted image of the sample 2 (for example, a 20°-tilted image) taken by illuminating the electron beam EB on a region of the sample 2 different from the region having resulted in the 60°-tilted image from a direction tilted by 20° relative to a line normal to the membrane surface 3a of the lipid membrane 3 (step S22).

The 20°-tilted image is taken under the condition where the sample 2 held to the sample holder 15 is tilted by 20° by the sample stage 14. Consequently, the electron beam EB can be illuminated to the sample 2 from a direction tilted by 20° relative to the membrane surface 3a of the lipid membrane 3, and a 20°-tilted image is obtained.

The third image acquisition portion 210 takes in information about the 20°-tilted image taken in this way and obtains the 20°-tilted image.

Then, the second image acquisition portion 114 obtains a non-tilted image of the sample 2, taken by illuminating the electron beam EB on the region, from which the 20°-tilted image was taken, perpendicularly to the membrane surface 3a of the lipid membrane 3 (step S24).

The 60°-tilted image and the 20°-tilted image may be identical in field of view.

Then, the orientation identification portion 116 identifies the orientations of the membrane proteins 4 of the 60°-tilted image on a basis of the non-tilted image (step S14).

Then, the orientation identification portion 116 identifies the orientations of the membrane proteins 4 in the 20°-tilted image on a basis of the non-tilted image (step S26). The processing of the step S26 is carried out in the same way as in the processing of the step S14.

Then, the 3D image reconstructing portion 118 first extracts images (60° particle images) of particles of the membrane proteins 4 from the obtained 60°-tilted image, classifies the extracted 60° particle images according to the orientations of the particles of the membrane proteins 4 while taking account of information about the orientations of the particles of the membrane proteins 4 identified by the orientation identification portion 116 (step S28), and averages the classified 60° particle images, i.e., 60° particle images of the membrane proteins 4 whose particles are identical or close in orientation (step S30). Similarly, the three-dimensional image reconstructing portion 118 classifies the obtained 20°-tilted images (second tilted images) (step S32) and averages them (step S34). Then, the 3D reconstructing portion 118 is analyzed to give a three-dimensional structural model of the membrane proteins 4, using the 60° particle images and 20° particle images averaged for each orientation of the particles of the membrane proteins 4 (step S18). Then, the 3D image reconstructing portion 118 makes a decision as to whether the reconstructed three-dimensional structural model needs to be refined (step S19). If the decision is that refinement is needed (if Yes at step S19), control returns to step S14, and processing of steps S14-S19 is performed. If the decision is that no refinement is needed (if No at step S19), the processing is ended. If membrane proteins 4 whose morphologies have slightly varied are contained, the 3D image constructing portion 118 can classify the tilted images precisely by comparing the obtained 60°-tilted images and 20°-tilted images.

Because of the steps described so far, a three-dimensional structural model of the membrane proteins 4 can be obtained.

The three-dimensional image construction method and image processor 200 associated with the second embodiment have the following effects, in addition to effects similar to the three-dimensional image construction method and image processor 100 associated with the first embodiment.

The three-dimensional image reconstruction method associated with the second embodiment comprises the step (step S22) of obtaining the second tilted images of the sample 2 taken by illuminating the electron beam EB on the sample 2 from a direction tilted at an angle different from that assumed when the first tilted images were taken relative to the line normal to the membrane surface 3a of the lipid membrane 3 and the step (step S24) of identifying the orientations of the membrane proteins 4 in the second tilted images on a basis of the non-tilted images. In the step (step S18) of reconstructing a three-dimensional structural model of the membrane proteins 4, a three-dimensional structural model of the membrane proteins 4 is reconstructed from the first and second tilted images, based on information about the identified orientations of the membrane proteins 4. Therefore, in the three-dimensional image reconstruction method associated with the second embodiment, a three-dimensional structural model can be constructed using a plurality of tilted images which are different in tilt angle (angle of incidence of the electron beam EB). Consequently, a high-resolution three-dimensional structural model can be built up at higher accuracy.

The image processor 200 includes the third image acquisition portion 210 for obtaining the second tilted images of the sample 2. The orientation identification portion 116 identifies the orientations of the membrane proteins 4 in the second tilted images, based on the non-tilted image. The 3D image reconstructing portion 118 is analyzed to give a three-dimensional structural model of the membrane proteins 4 from the first tilted images and the second tilted images on a basis of information about the identified orientations of the membrane proteins 4. Therefore, the image processor 200 can construct a higher-resolution three-dimensional structure.

In the second embodiment, a three-dimensional structural model of the membrane proteins 4 is reconstructed from the 60°-tilted image and 20°-tilted image. Alternatively, a three-dimensional structural model may be reconstructed also by including tilted images of other angles. For example, a three-dimensional structural model may be reconstructed from a 60°-tilted image, a 45°-tilted image, a 20°-tilted image, and a 0°-tilted image (non-tilted image).

The present invention embraces configurations (e.g., configurations identical in function, method, and results or identical in purpose and advantageous effects) which are substantially identical to the configurations described in the embodiments. Furthermore, the invention embraces configurations which are similar to the configurations described in the embodiments except that their nonessential portions have been replaced. Additionally, the invention embraces configurations which are identical in advantageous effects to, or which can achieve the same object as, the configurations described in the embodiments. Further, the invention embraces configurations which are similar to the configurations described in the embodiments except that a well-known technique is added.

EXPLANATION OF SYMBOLS

2: sample; 3: lipid membrane; 4: membrane proteins; 5: carbon film; 10: electron microscope body; 11: electron beam source; 12: condenser lenses; 13: objective lens; 14: sample stage; 15: sample holder; 16: intermediate lens; 17: projector lens; 18: imaging portion; 20: vibration isolators; 22: pedestal; 100: image processor; 110: processing section; 112: first image acquisition portion; 114: second image acquisition portion; 116: orientation identification portion; 118: 3D image constructing portion; 120: manipulation portion; 122: display portion; 124: storage portion; 126: information storage medium; 200: image processor; 210: third image acquisition portion; 1000: electron microscope; 2000: electron microscope

The invention claimed is:

1. A three-dimensional image reconstruction method of reconstructing a three-dimensional structural model of membrane proteins, said method comprising the steps of:
   obtaining, with a field of view, a first transmission electron microscope image of a sample taken by illuminating an electron beam on the sample containing the membrane proteins present within a lipid membrane from a direction tilted relative to a line normal to a membrane surface of the lipid membrane;
   obtaining, with a field of view that at least partially overlaps the field of view used to obtain the first transmission electron microscope image, a second transmission electron microscope image of the sample taken by illuminating the electron beam on the sample perpendicularly to the membrane surface of the lipid membrane;
   identifying orientations of a plurality of particles of the membrane proteins in the first transmission electron microscope image on a basis of a rotational angle of the plurality of particles relative to an axis perpendicular to the lipid membrane of the corresponding plurality of particles of the membrane proteins in the second transmission electron microscope image; and
   constructing a three-dimensional structure of the membrane proteins by:
      extracting a plurality of particle images of the membrane proteins from the first transmission electron microscope image,
      classifying the extracted images according to the orientations of the plurality of particles of the membrane proteins identified in the step of identifying orientations of the membrane proteins,
      averaging the classified particle images for each of a plurality of orientations of the membrane proteins, and
      generating, based on the average of each classified particle image, a three-dimensional image of the membrane proteins.

2. The three-dimensional image reconstruction method of claim 1, further comprising the steps of:
   obtaining, with a field of view that at least partially overlaps the field of view used to obtain the first and second transmission electron microscope images, a third transmission electron microscope image of said sample taken by illuminating said electron beam on said sample from a direction tilted at an angle different from that assumed when said first transmission electron microscope image was taken relative to the line normal to the membrane surface of said lipid membrane; and
   identifying orientations of a plurality of particles of the membrane proteins in the third transmission electron microscope image on a basis of a rotational angle of the plurality of particles relative to an axis perpendicular to the lipid membrane of the corresponding plurality of particles of the membrane proteins in said second transmission electron microscope image;
   wherein, in the step of constructing a three-dimensional structure of the membrane proteins, the three-dimensional structure of the membrane proteins is reconstructed from the first transmission electron microscope and the third transmission electron microscope image on a basis of information about the identified orientations of the membrane proteins.

3. The three-dimensional image reconstruction method of claim 1, wherein the dose of said electron beam on the sample assumed when said second transmission electron microscope image is taken is greater than the dose of the electron beam on the sample assumed when said first transmission electron microscope image is taken.

4. The three-dimensional image reconstruction method of claim 1, wherein said second transmission electron microscope image is taken after said first transmission electron microscope image is taken.

5. An image processor for constructing a three-dimensional structure of membrane proteins, comprising:
   a first image acquisition portion for obtaining, with a field of view, a first transmission electron microscope image of a sample containing said membrane proteins present within a lipid membrane, the image having been taken by illuminating an electron beam on the sample from a direction tilted relative to a line normal to a membrane surface of the lipid membrane;

a second image acquisition portion for obtaining, with a field of view that at least partially overlaps the field of view used to acquire the first transmission electron microscope image, a second transmission electron microscope image of the sample, the second transmission electron microscope image having been taken by illuminating the electron beam on the sample perpendicularly to the membrane surface of the lipid membrane;

an orientation identification portion for identifying orientations of a plurality of particles of the membrane proteins in the first transmission electron microscope image on a basis of a rotational angle of the plurality of particles relative to an axis perpendicular to the lipid membrane of the corresponding plurality of particles of the membrane proteins in the second transmission electron microscope image; and a 3D image constructing portion for reconstructing a three-dimensional structure of the membrane proteins by:
- extracting a plurality of particle images of the membrane proteins from the first transmission electron microscope image,
- classifying the extracted images according to the orientation of the plurality of particles of the membrane proteins identified by the orientation identification portion,
- averaging the classified particle images for each of a plurality of orientations of the membrane proteins, and
- generating, based on the average of each classified particle image, a three-dimensional image of the membrane proteins.

6. The image processor of claim 5, further comprising a third image acquisition portion for obtaining, with a field of view that at least partially overlaps the field of view used to acquire the first and second transmission electron microscope images, a third transmission electron microscope image of said sample taken by illuminating the electron beam on said sample from a direction tilted at an angle different from that assumed when said first transmission electron microscope image was taken relative to the line normal to the membrane surface of said lipid membrane;
- wherein said orientation identification portion identifies orientations of a plurality of particles of the membrane proteins in the third transmission electron microscope image on a basis of a rotational angle of the plurality of particles relative to an axis perpendicular to the lipid membrane of the corresponding plurality of particles of the membrane proteins in said second transmission electron microscope image; and
- wherein said 3D image reconstructing portion is analyzed to give a three-dimensional structure of the membrane proteins from both said first transmission electron microscope image and said third transmission electron microscope image on a basis of information about the identified orientations of the membrane proteins.

7. An electron microscope including an image processor set forth in claim 5.

* * * * *